United States Patent
Kappel et al.

[11] Patent Number: 5,840,255
[45] Date of Patent: Nov. 24, 1998

[54] GAS SENSOR

[75] Inventors: Andreas Kappel; Randolf Mock, both of München; Hans Meixner, Haar, all of Germany

[73] Assignee: Siemens Aktiengesellschaft, Munich, Germany

[21] Appl. No.: 777,021

[22] Filed: Dec. 30, 1996

[30] Foreign Application Priority Data

Dec. 29, 1995 [DE] Germany .................. 195 49 146.7

[51] Int. Cl.⁶ ............................................ G01N 27/04
[52] U.S. Cl. .................. 422/90; 422/98; 338/34; 338/64
[58] Field of Search .............. 422/90, 98; 436/151, 436/152; 338/34, 64

[56] References Cited

U.S. PATENT DOCUMENTS

| | | |
|---|---|---|
| 4,361,539 | 11/1982 | Weinberg et al. .................. 422/98 |
| 4,387,165 | 6/1983 | Youngblood . |
| 4,889,611 | 12/1989 | Blough, Jr. ........................ 204/411 |
| 5,372,785 | 12/1994 | Johnson et al. . |

FOREIGN PATENT DOCUMENTS

| | | |
|---|---|---|
| 0 311 439 A2 | 4/1989 | European Pat. Off. . |
| 4339737 | 1/1995 | Germany . |
| 2 029 583 | 3/1980 | United Kingdom . |
| 2 142 147 | 1/1985 | United Kingdom . |

*Primary Examiner*—Jeffrey Snay
*Attorney, Agent, or Firm*—Herbert L. Lerner; Laurence A. Greenberg

[57] ABSTRACT

In order to avoid measurement signal drift, a gas sensor has a gas sensitive layer which is provided on its upper side with a measuring electrode structure and on its lower side with an electrically conductive layer.

19 Claims, 8 Drawing Sheets

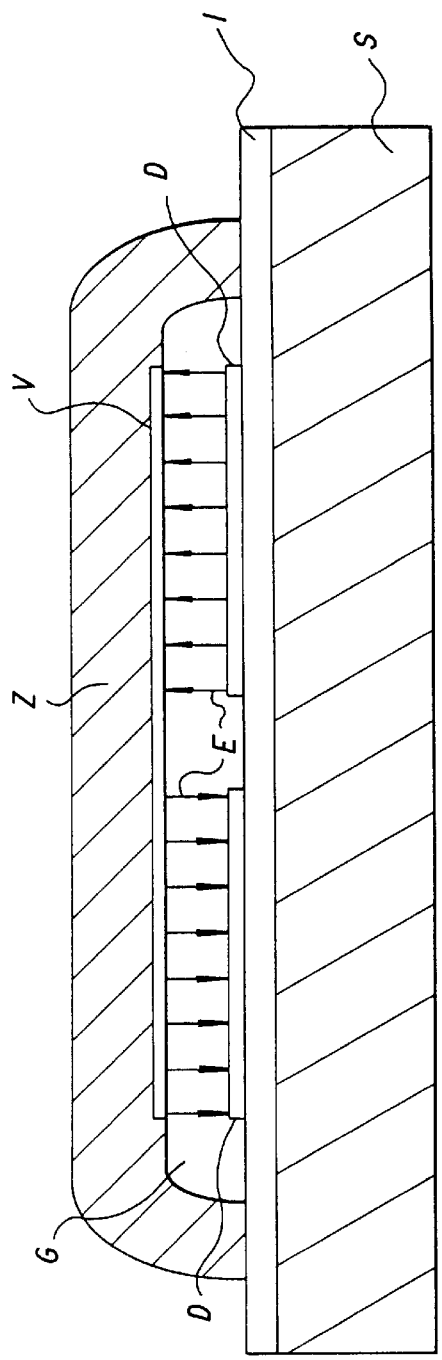
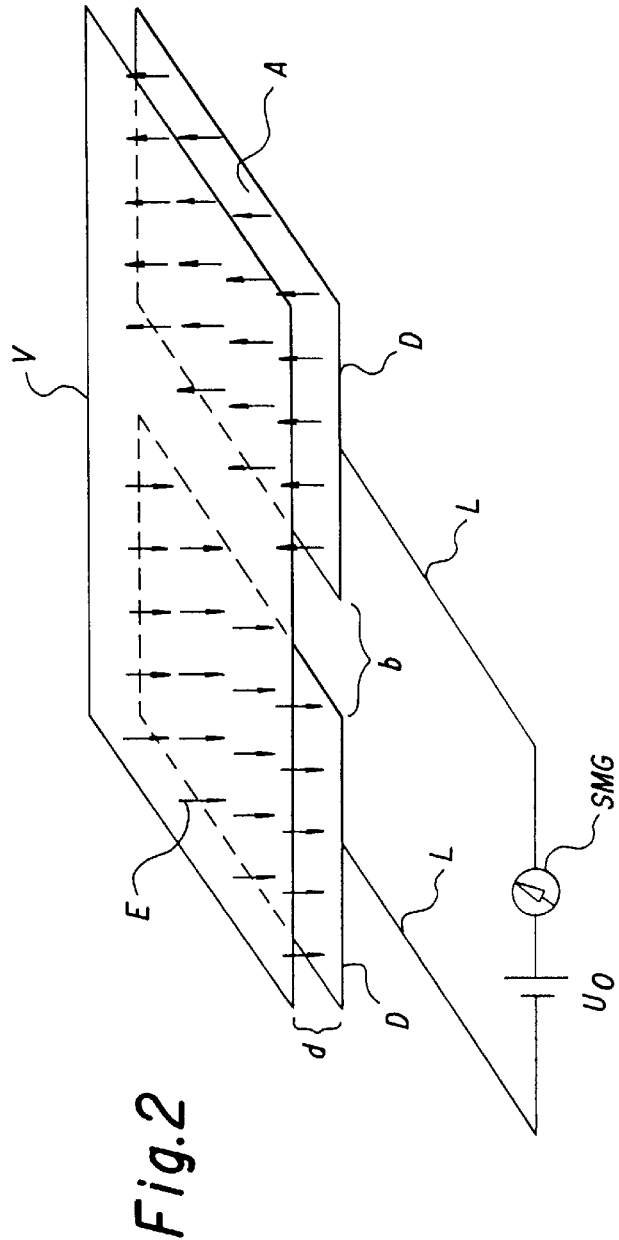
Fig.1
Fig.2

GAS SENSOR

BACKGROUND OF THE INVENTION

Field of the Invention

The invention relates to a gas sensor.

Resistive gas sensors are based on the property of special gas-sensitive materials. Their electrical property varies in a characteristic and replicable way in the presence of certain gases, as a function of their concentration. Detecting a change in conductivity of the gas-sensitive material is typically performed electrically. To that end, the gas-sensitive material is connected to an electrical voltage source, for instance, through the use of measuring electrodes, in such a way that an electrical current circuit is the result.

If resistive gas sensors are used in the exhaust tract or pipe of an internal combustion engine in order to detect the presence of certain gases there, then the resistive gas sensor must be protected against mechanical and chemical factors. That can be achieved through the use of an at least partially gas-permeable protective layer (sacrificial layer), which is applied to the gas-sensitive element. In that respect, see German Patent DE 43 39 737 C1. Since the protective layer in turn can have an electrical conductivity and moreover may itself be gas-sensitive, the result is an undesired, poorly controllable electric parallel resistor to the actual sensor resistor. Moreover, under the influence of the attacking media, the protective layer can change both its chemical composition and its electrical conductivity, which can additionally make itself felt in a driftlike change in the characteristic curve of the sensor. The resistance of the protective layer is moreover highly temperature-dependent. Therefore, the influence of the protective layer on the measurement accuracy is also highly temperature-dependent.

In order to attain a stable or in other words drift-free sensor signal, the sensor temperature must therefore be adhered to exactly and constantly, which under typical ambient conditions, such as high-speed gas streams in the exhaust tract, is extraordinarily difficult and in each case necessitates rapid, precise temperature regulation.

SUMMARY OF THE INVENTION

It is accordingly an object of the invention to provide a gas sensor, which overcomes the hereinafore-mentioned disadvantages of the heretofore-known devices of this general type and in which sensor drift is minimized.

With the foregoing and other objects in view there is provided, in accordance with the invention, a gas sensor, comprising a gas sensitive layer having two sides; a measuring electrode structure on one of the sides of the gas sensitive layer; and an electrically conductive layer on the other of the sides of the gas sensitive layer.

Effects such as a change in the external electrical field no longer have any influence on the measurement accuracy.

The influence of the protective layer on the measurement accuracy is likewise minimized.

In accordance with another feature of the invention, there is provided a substrate carrying the measuring electrode structure, the gas sensitive layer, and the electrically conductive layer. This has the advantage of increased mechanical stability.

In accordance with a further feature of the invention, there is provided an insulation layer between the measuring electrode structure and the substrate, in order to reduce the influence of the substrate on the measurement accuracy.

In accordance with an added feature of the invention, there is provided a protective layer coating the gas sensitive layer and the electrically conductive layer, in order to protect the gas sensitive layer against chemical factors.

In accordance with another feature of the invention, the gas sensitive layer includes a substance selected from the group consisting of strontium titanate, barium titanate, vanadium oxide, gallium oxide, cerium oxide, barium stannate and zinc oxide.

In accordance with yet another feature of the invention, the electrically conductive layer includes a catalytically active material. This gas sensor structure has the advantage of permitting the characteristic of the gas sensor, that is the sensitivity and the cross-sensitivity to certain types of gases, to be varied and set purposefully through the use of a suitable choice of catalyst. Moreover, the steepness of the sensor characteristic curve can be varied through the use of the catalyst.

In accordance with yet a further feature of the invention, the electrically conductive layer includes a substance selected from the group consisting of a metal oxide, a ceramic and an organic material. This gas sensor structure has the advantage of great universality, since instead of a typically purely metal electrically conductive layer, for instance, metal oxides and ceramics or even organic substances such as phthalocyanin can be used. Metal oxides and ceramics, for instance, are distinguished by a very high temperature resistance. On the other hand, by using organic materials, chemical reactions can be catalyzed purposefully, and their reaction products can in turn be evidenced by the gas sensitive layer. The top electrode on the other hand can also have a filtering effect, so that only certain types of gases can penetrate the top electrode and be detected by the gas sensitive layer. This can, for instance, improve the selectivity of the sensor.

In accordance with yet an added feature of the invention, the electrically conductive layer has a porous or perforated structure. This is done in order to increase the measurement speed. The access of gas to the gas sensitive layer is also increased.

In accordance with still a further feature of the invention, the protective layer includes a substance selected from the group consisting of strontium titanate, barium titanate, vanadium oxide, gallium oxide, cerium oxide, barium stannate and zinc oxide.

In accordance with still an added feature of the invention, the protective layer and the gas sensitive layer include the same material.

In accordance with yet an additional feature of the invention, a heater is provided in order to increase the measurement accuracy and the sensitivity.

In accordance with again another feature of the invention, there is provided at least one further gas sensitive layer disposed above the electrically conductive layer; and at least one further electrically conductive layer disposed above the at least one further gas sensitive layer. In accordance with again an added feature of the invention, there is provided at least one further gas sensitive layer and at least one further electrically conductive layer disposed between the electrically conductive layer and the protective layer. In accordance with again an additional feature of the invention, the at least one further gas sensitive layer includes a substance selected from the group consisting of strontium titanate, barium titanate, vanadium oxide, gallium oxide, cerium oxide, barium stannate and zinc oxide. In accordance with still another feature of the invention, the at least one further electrically conductive layer includes a substance selected from the group consisting of a metal oxide, a ceramic and an organic material. In such a gas sensor, the advantages of a long current path can be combined with the possibilities of various materials for the individual horizontal layers of the shielding electrodes, the bottom electrode and the individual gas sensitive layers.

In accordance with a concomitant feature of the invention, the at least one further electrically conductive layer has a porous or perforated structure.

Other features which are considered as characteristic for the invention are set forth in the appended claims.

Although the invention is illustrated and described herein as embodied in a gas sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a diagrammatic, cross-sectional view showing a basic layout of the sensor of the invention;

FIG. 2 is a perspective view of electrodes of the sensor of the invention;

Description OF THE PREFERRED EMBODIMENTS

Referring now to the figures of the drawings in detail and first, particularly, to FIG. 1 thereof, there is seen a sensor of the invention, that is shown in cross section and has a substrate S above which an electric insulation layer I is provided. The presence of the electric insulation layer I is optional and is necessary only in the case of a substrate S with its own interfering conductivity. As can also be seen from FIG. 1, measuring electrodes D and a gas sensitive layer G are disposed on the insulation layer I. The gas sensitive layer G is provided partially, as seen in FIG. 1, or entirely, with a shielding electrode V, which is also referred to below as an electrically conductive layer. A protective layer Z is applied over the shielding electrode V.

The presence of the protective layer Z is not absolutely necessary. The decision as to whether or not the protective layer Z must be present and to what thickness it should be made, depends on the particular intended application of the sensor.

The sensor should be provided with a heating configuration, depending on the application, although this is not shown in FIG. 1.

The shielding electrode V (which is also referred to below as the shielding layer) acts as an equipotential surface for an electrical field E above the measuring electrodes D, which are also referred to as bottom electrodes herein. The shielding electrode V completely electrically shields (=Faraday shielding) the electrical field E from the external space and in particular from the region of the protective layer Z, if it is present. The shielding electrode V has no electrical terminals.

In order to illustrate the mode of operation of the gas sensor of the invention, FIG. 2 shows the measuring electrodes D and the shielding electrode V of the sensor in a perspective view, wherein reference symbol L indicates supply leads to the measuring electrodes D. The leads L are connected to a supply voltage source, which generates a voltage $U_0$, and to a current meter SMG. After the application of the voltage $U_0$, the electrical field E develops between the measuring electrodes D and the shielding electrode V.

The disposition of the bottom electrodes D and the shielding electrode V is essentially equivalent to that of two series-connected plate capacitors with a plate spacing d and a gas-sensitive, electrically conductive dielectric, which in this case represents the gas sensitive layer G. The electrical field E is therefore limited to the regions between the measuring electrodes D and the shielding electrode V. As a result, the vector of the intensity of the electrical field E (with the exception of the peripheral regions, which can be ignored) is orthogonal to the electrode surfaces. The current, which is created in the electrical circuit by the voltage source and is a measure for the gas concentration, and its changes, is indicated or displayed through the use of the current meter SMG.

Figure 3:
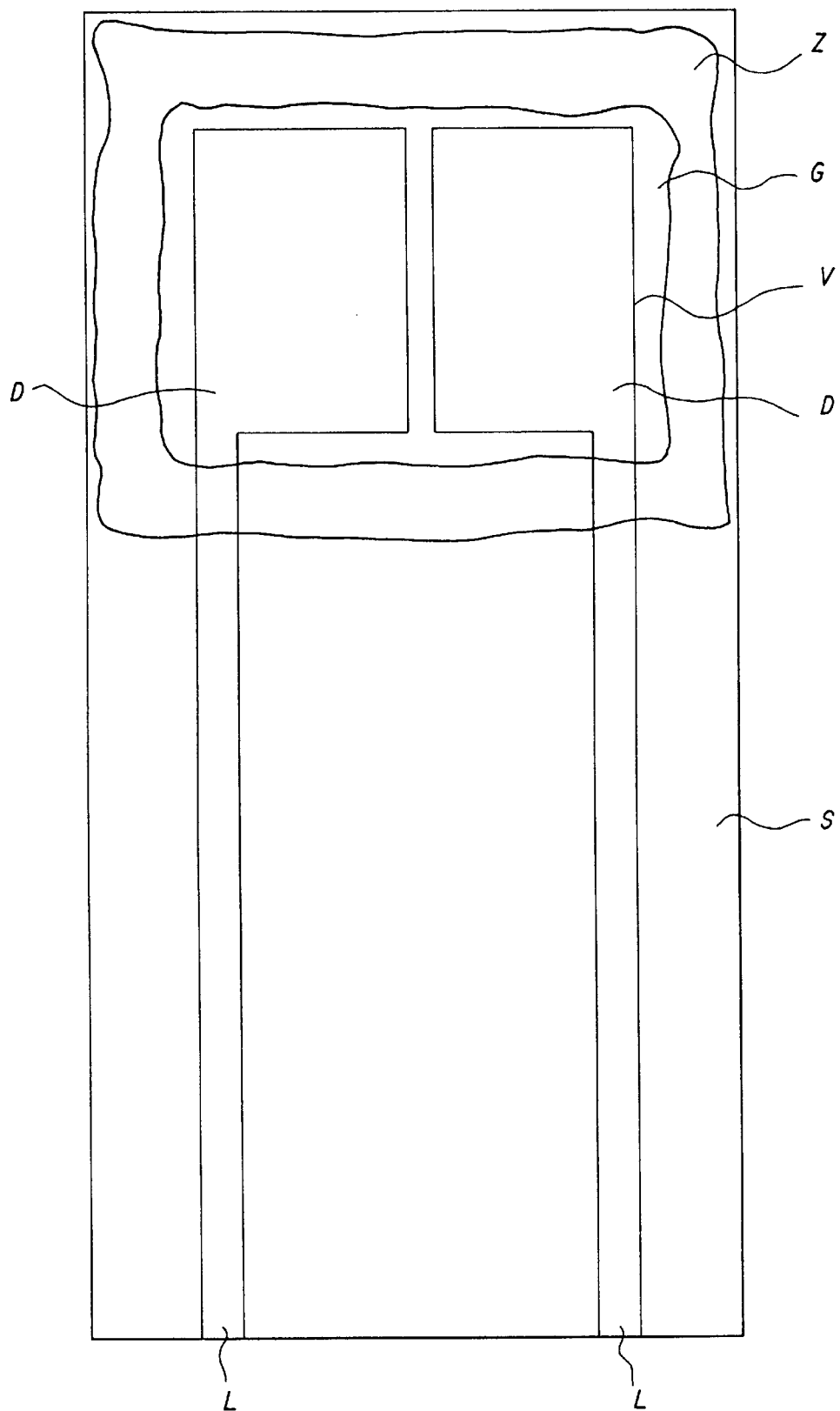
FIG. 3 is a plan view of the sensor of the invention.

The plan view of the sensor is shown in FIG. 3. The generally flat bottom electrodes D are located on the surface of the substrate S, which under some circumstances is provided with an insulation layer I that is not shown in FIG. 3. The conductor tracks or leads L, with which the measuring electrodes D are connected, are used for supplying current. The gas sensitive layer G is located between the measuring electrodes D and the gas-permeable shielding electrode V that is disposed above the measuring electrodes D.

In order to protect the sensor, the active sensor region is covered with the gas-permeable protective layer Z.

The sensor heater is expediently disposed on the back side of the substrate S in the region of the active sensor material or layer G and is dimensioned in such a way that the most homogeneous possible temperature distribution is achieved in this region.

In order to protect the supply lines or conductor tracks L, for instance against oxidation and chemical and mechanical attack, the conductor tracks L may be provided with an additional cover layer that is not shown in the drawings.

Due to the disposition of the shielding electrode V above the measuring electrodes D, the following advantages are attained:

1. The sensor can be constructed with very low impedance, thereby greatly reducing problems that would otherwise be caused by electrical interference and electrical parallel resistances.

On the condition that a lateral spacing b of the measuring electrodes D from one another (as seen in FIG. 2) is substantially greater than the spacing d, that is, b >>d, the following equation applies for the sensor resistance:

$$R_s = \rho \cdot \frac{d}{A} \ [\Omega]$$

wherein

ρ=specific electrical resistance of the gas-sensitive material G (in Ωm), and

A=area of the top side or surface of a measuring electrode D (in m$^2$).

2. The sensor area can be reduced considerably, which makes it possible to reduce the heating output and additionally greatly facilitates a homogeneous temperature distribution in the region of the gas-sensitive material G.

3. The demands in terms of production technology are markedly less because of the coarse electrode structures that are now possible. This makes it possible, for instance, to use a less stringent category of clean room and a simple structuring technique, such as lift-off molding.

4. Changes in the electrical conductivity of the protective layer V resulting, for instance, from a gradual chemical conversion of the protective layer (oxidation, nitriding, etc.) in long-term operation, due to mechanical abrasion or contamination of the surface (such as with abrasion particles or condensed water), have no effects on the electrical sensor signal.

5. The gas-sensitive properties of the sensor can be influenced purposefully by catalytically active materials for the shielding electrode V, and in these cases the electrical shielding action may also be of secondary importance under some circumstances.

6. Not only can metals and metal compounds be used for the shielding electrode V, but in general materials having an electrical conductivity which is so high in relation to that of the protective layer Z that an adequate electrical Faraday shielding can be attained. This includes all adequately electrically conductive inorganic elements and compounds (such as metal oxides, ceramics, semiconductors) and organic elements and compounds (such as phthalocyanin).

7. The shielding electrode V can in turn include a multilayer or multiply system, such as an electrically conductive layer or ply that acts to provide the Faraday shielding, and a catalytically active layer or ply.

Adequate gas permeability of the shielding electrode V can be attained in various ways:

I. Structuring (photo and etching techniques) of a shielding electrode V precipitated out over the entire surface, thereby creating free regions (perforated, gridlike or striplike structures) through which the gas passage/gas diffusion can occur, as is seen in see FIGS. 4 and 5.

Figure 4:
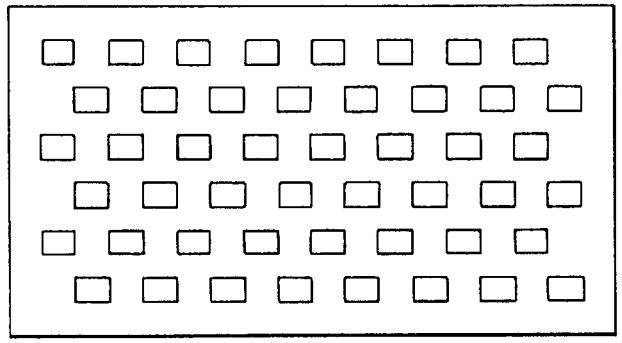
FIG. 4 is an elevational view of a first possible embodiment of the shielding layer.
Figure 5:
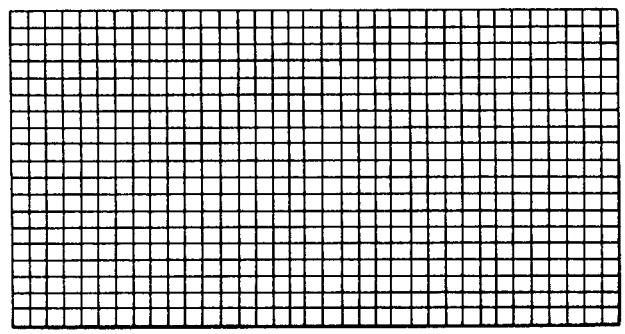
FIG. 5 is an elevational view of a second possible embodiment of the shielding layer.

II. Structured application of the shielding electrode V, for instance by screenprinting techniques, in the form of perforated, gridlike or striplike structures, as is seen in FIGS. 4 and 5.

III. Full-surface application of such a thin layer for the shielding electrode V, for instance by sputtering or vapor deposition, that adequate diffusion of gas molecules through the shielding electrode V is possible.

Figure 6:
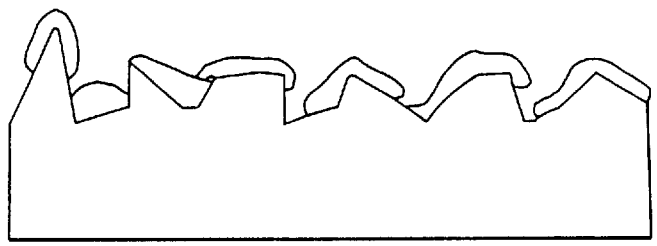
FIG. 6 is an elevational view of a third embodiment of the shielding layer.

IV. Full-surface application of such a thin layer for the shielding electrode V which is made, for instance, by sputtering or vapor deposition, in relation to the surface topography of the gas sensitive layer G that is produced, for instance by screenprinting, that the result is a structure which while cohesive is nevertheless highly gas-permeable because of poor edge coverage. In this respect, see FIG. 6.

An especially low-impedance sensor resistor can be attained in this case as well by using so-called interdigital structures, that is structures meshing with one another in comblike fashion, for the measuring electrodes D. The interdigital electrodes can be used both to supply power and to tap potential. Typically, prong spacings of the electrodes are from 1 µm to 100 µm.

Low-impedance metal elements or metal compounds are used for the measuring electrodes V.

The shielding electrode V can also be closed, although this is not shown in the drawings. A diffusion through the shielding electrode V, which in this case is also a gas entry to the gas sensitive layer G, is also possible.

Figure 7:
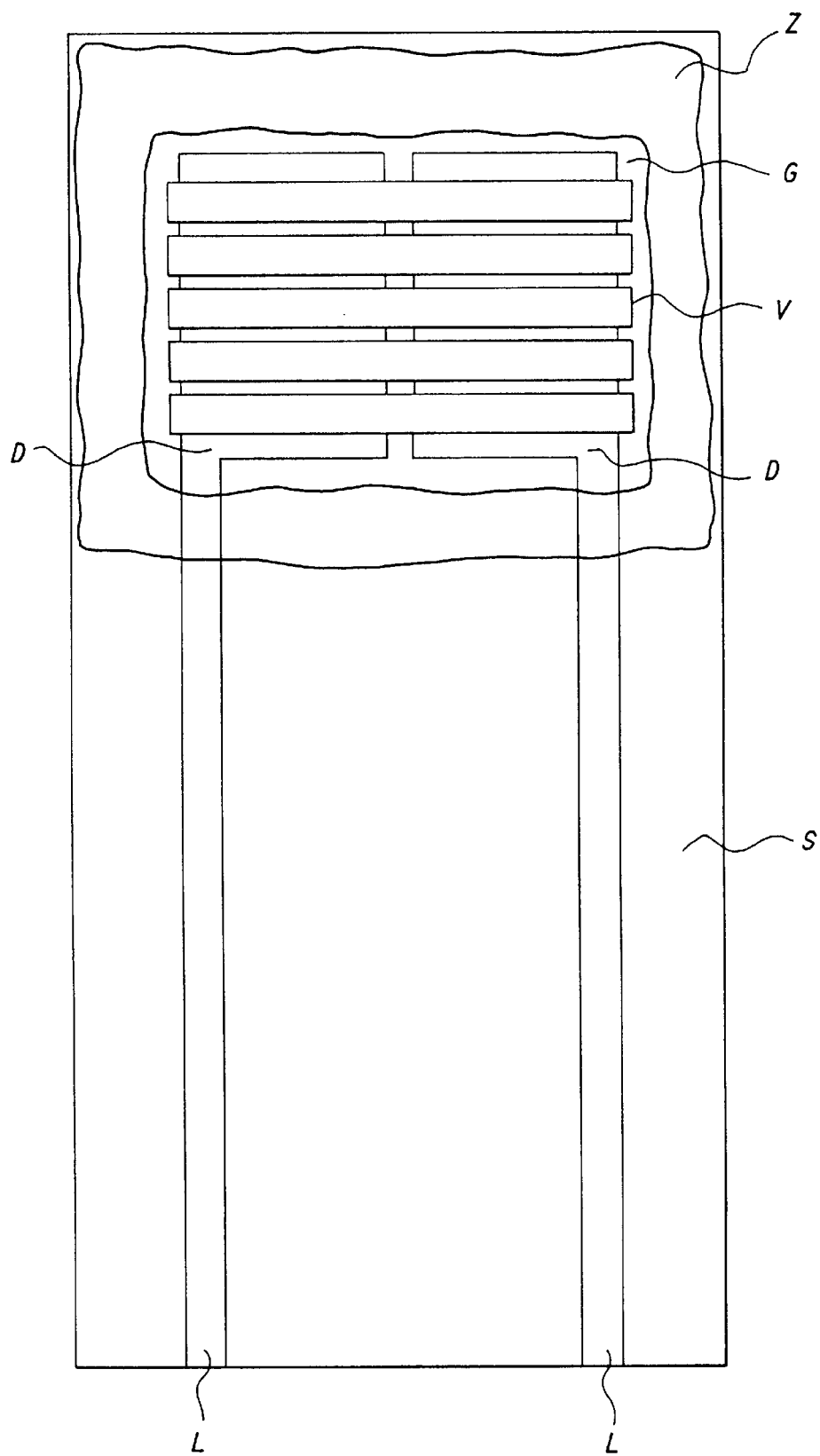
FIG. 7 is a plan view in which a top electrode is constructed in striplike fashion.

In the exemplary embodiment shown in FIG. 7, the electrically conductive shielding electrode V has striplike conductor tracks. These tracks are disposed above the bottom electrodes D in such a way that large regions of the bottom electrodes D are covered by each individual conductor track of the shielding electrode V, and a flow of current from one of the bottom electrodes D through the gas-sensitive material G into the striplike conductors of the shielding electrode V and from there in turn through the gas sensitive layer G into the other portion of the bottom electrode D, is possible. Moreover, the individual striplike conductor tracks of the shielding layer V are disposed with a certain spacing from one another, so that good gas passage is possible through interstices between the individual conductor tracks of the shielding electrode to the gas sensitive layer G located beneath. Along with its simple structure, the layout shown in FIG. 7 is additionally distinguished by good response performance.

Figure 8:
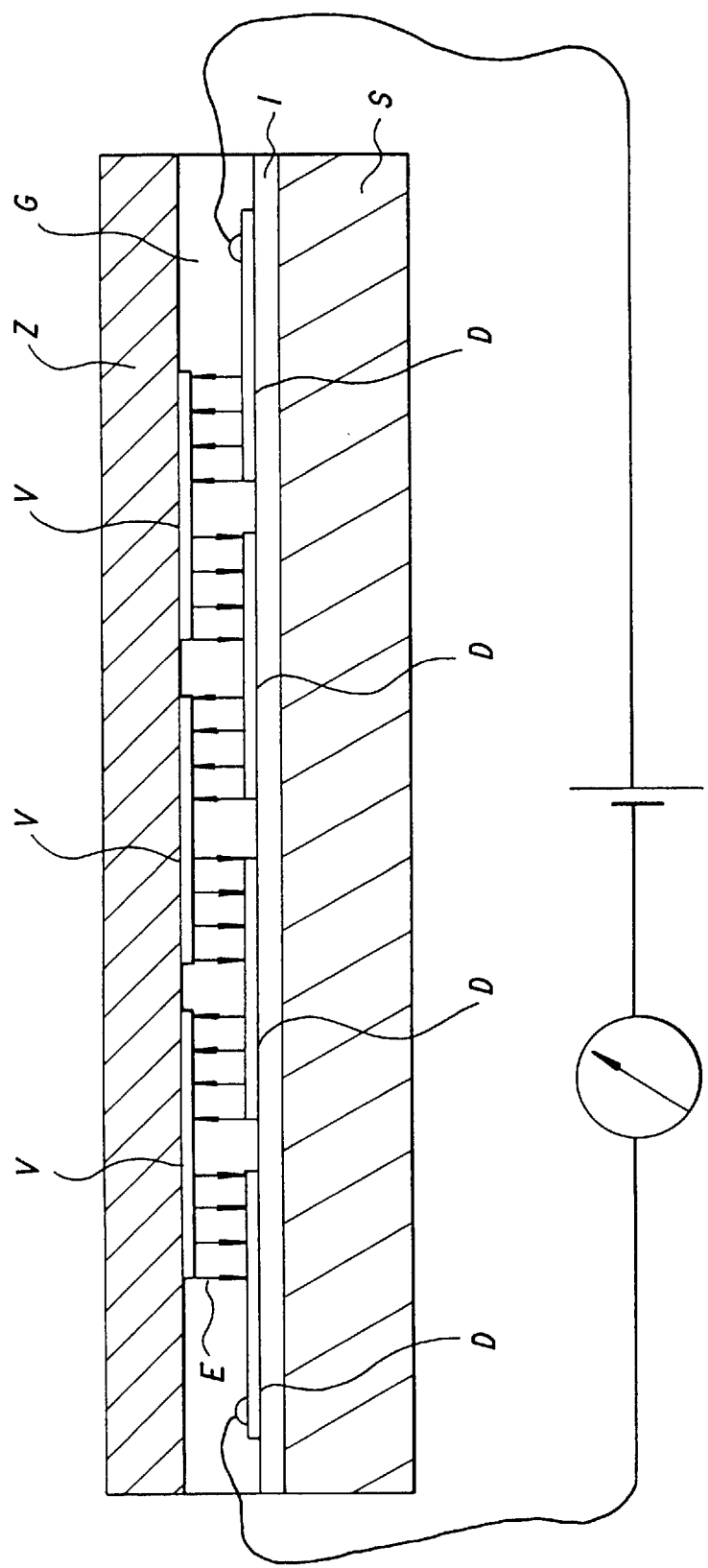
FIG. 8 is a view similar to FIG. 1 of another embodiment of the gas sensor, in which both a bottom electrode and the top electrode have a plurality of conductor tracks.

As FIG. 8 shows, it is possible, by a sequential configuration of the conductor tracks of the bottom electrode D and the conductor tracks of the shielding electrode V in overlapping form, to substantially lengthen the current path in the gas-sensitive material G, as compared with the exemplary embodiments shown in FIGS. 1–3. As a result, a higher sensor resistance can be achieved in a simple way. This can be advantageous in the case of very low-impedance gas-sensitive materials for the gas sensitive layer G. At the same time, because of the striplike, interrupted configuration of the shielding electrode V, good gas access to the gas sensitive layer is assured.

Figure 9:
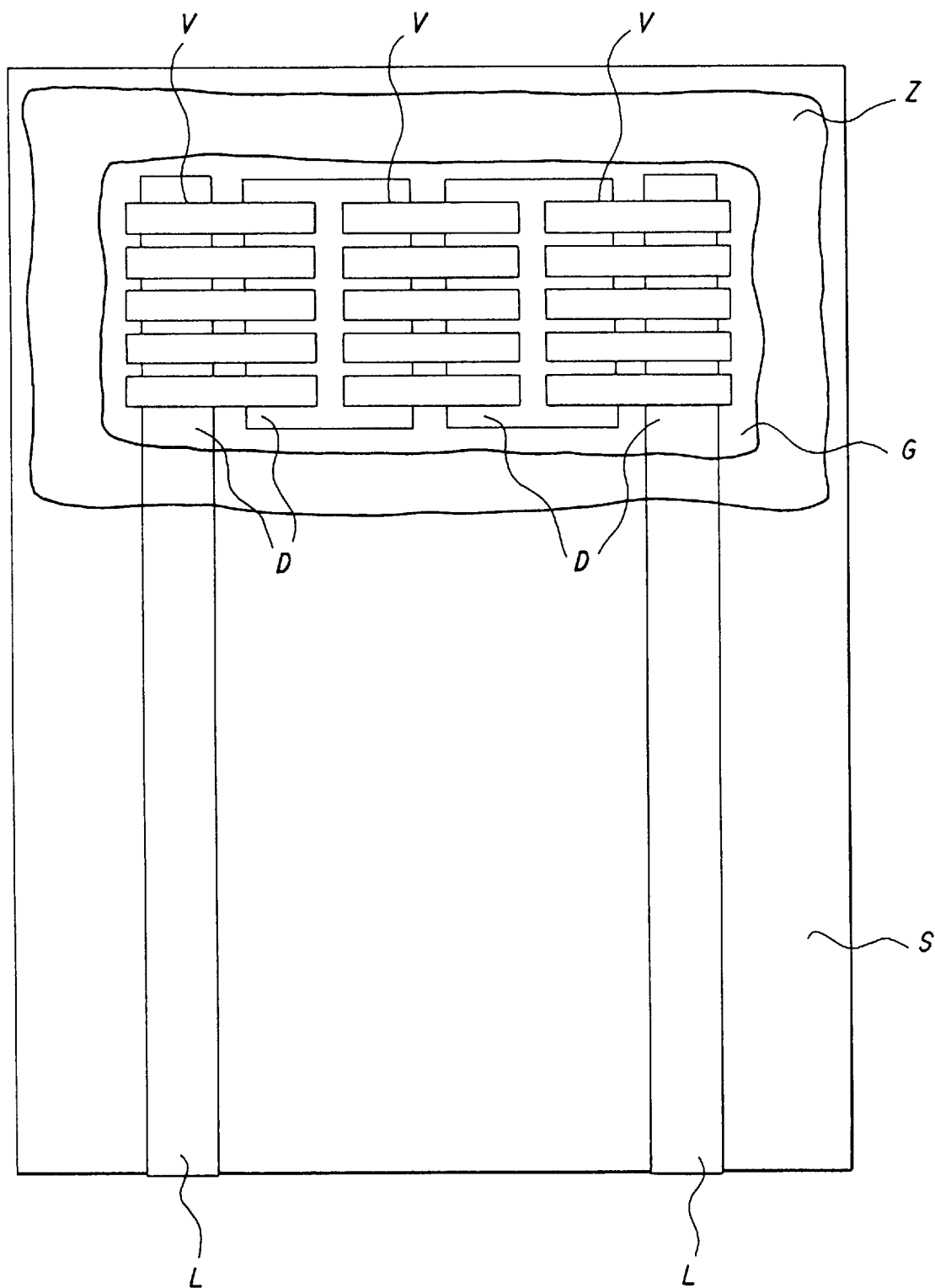
FIG. 9 is a plan view of the embodiment of the gas sensor shown in FIG. 8.

FIG. 9 shows a plan view of a gas sensor which is assembled according to the principle described with regard to FIG. 8, with a bottom electrode D that has four conductor tracks. The shielding electrode V is divided into three regions, which in turn include striplike conductor tracks (that is, conductors). The mode of operation is equivalent to the configuration shown in FIG. 3.

Figure 10:
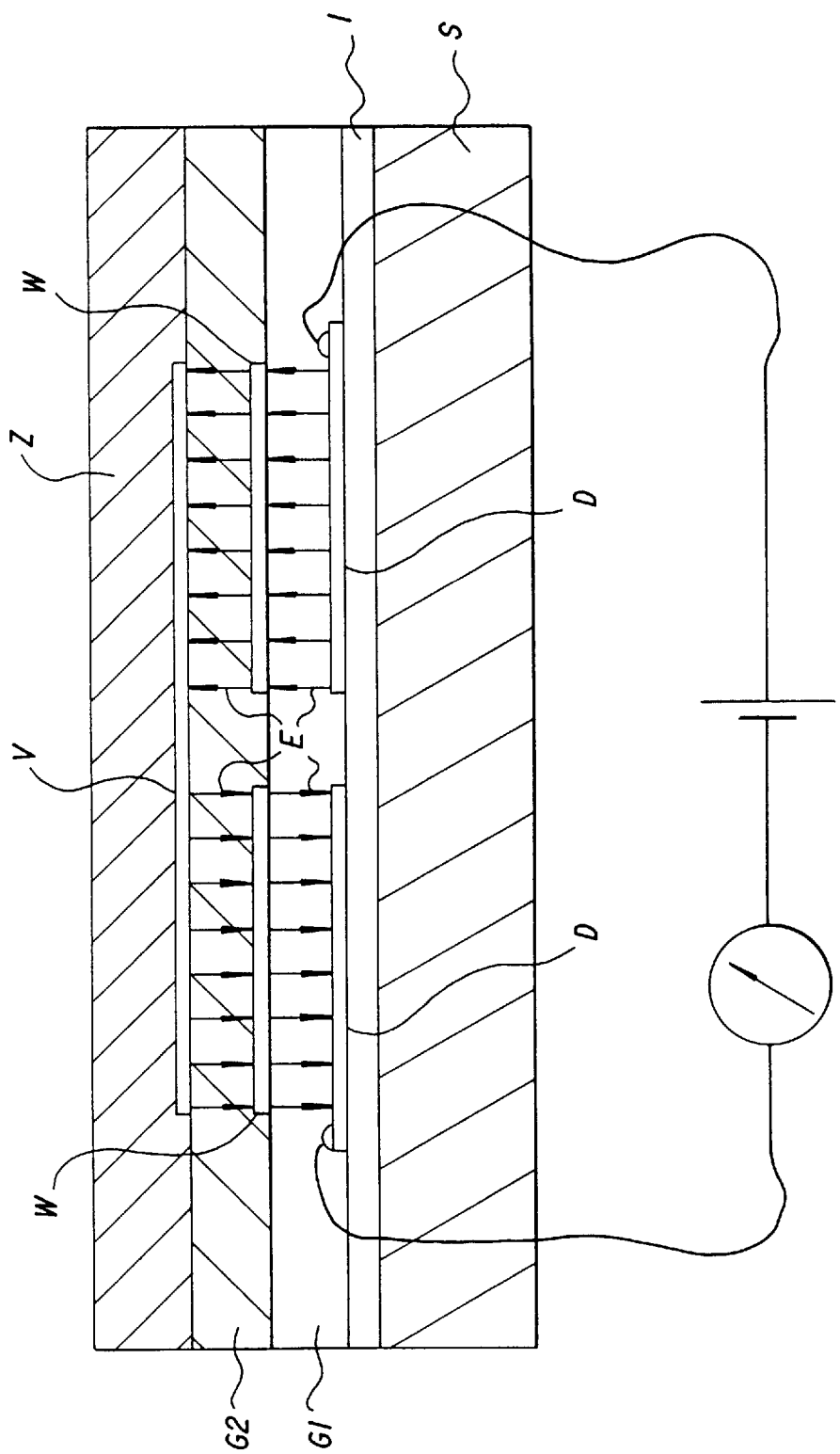
FIG. 10 is another view similar to FIG. 1 of a further embodiment of the gas sensor, in which a gas sensitive layer is applied in two layers, and a second shielding electrode is incorporated between those two layers.

Along with the various possibilities of horizontal disposition of the bottom electrode D and individual regions of the shielding electrode V, as have been described in the previous exemplary embodiments, the shielding electrode V can also be vertically layered in various ways. One exemplary embodiment of this is shown in FIG. 10. The sensor properties can be varied or adapted purposefully to given requirements in wide regions by using various materials for electrodes D, W and V, and in particular by using different gas-sensitive materials for layers G1 and G2 and different layer thicknesses for these layers G1 and G2.

Gas sensors with entirely novel sensor characteristics can be produced by combining various gas sensitive layers in a single sensor. Through the use of an additional striplike embodiment of the individual conductor tracks of the shielding electrode V, in addition to the type already shown (see FIGS. 7 and 9), the gas access can also be improved in this case and therefore the response speed can be increased.

Figure 11:
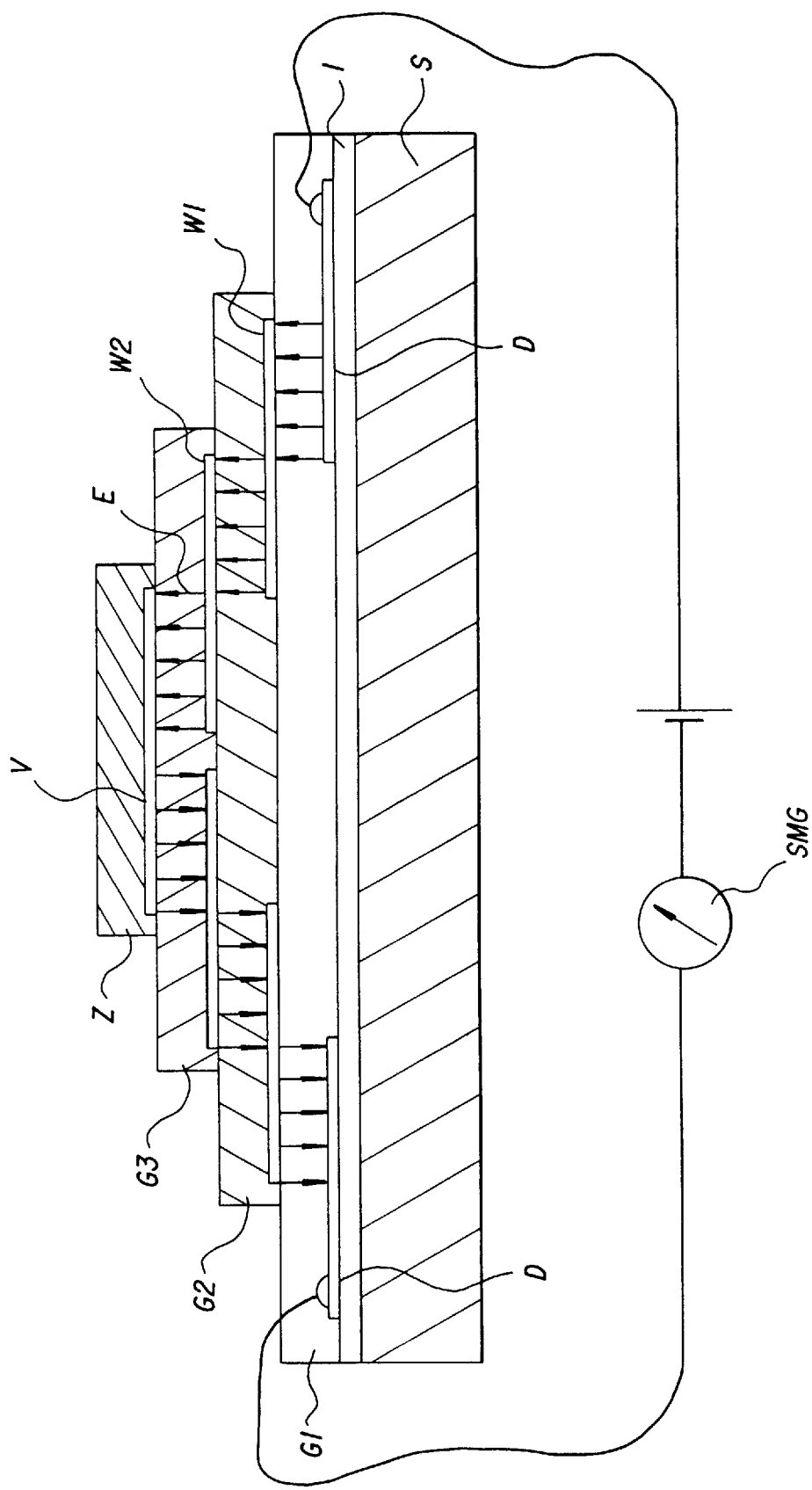
FIG. 11 is an additional view similar to FIG. 1 of a further embodiment of the gas sensor, in which the gas sensitive layer has three layers and is disposed in stairstep fashion, and shielding electrodes are incorporated between each two layers.

It is finally possible to achieve configurations as shown in FIG. 11 by vertically staggering overlapping conductor tracks of the bottom electrode D and through the use of various shielding electrode structures V, W1, W2. As a result, the advantages of a long current path can be combined with good gas access and the possibilities of various materials for the individual horizontal layers of the shielding electrodes W1, W2, the bottom electrode D, and the top electrode V and for individual gas sensitive layers G1, G2 and G3.

As compared with the exemplary embodiment shown in FIG. 10, the gas access particularly to the lower gas sensitive layers G1 and G2 is improved substantially, because of the stairsteplike geometry.

The overlapping of the individual gas sensitive layers G1, G2 and G3 is moreover selected in such a way that whichever layer is on top acts as a protective layer for the gas sensitive layer beneath it. In other words, a layer Z acts to protect an active region of the gas sensitive layer G3. The gas sensitive layer G3 serves to protect an active region of the gas sensitive layer G2, and the gas sensitive layer G2 serves to protect an active region of the gas sensitive layer G1.

In order to further increase the response speed, once again the individual shielding electrodes V, W2 and W1 can be constructed in striplike fashion, in addition to the type already shown.

The number of individual gas sensitive layers of the exemplary embodiments shown in FIGS. 10 and 11 is unlimited in principle.

Faraday shielding of the active regions of the gas-sensitive material from external electrical fields is assured in the same way, in all of the exemplary embodiments that are presented. Gas sensors with entirely novel sensor characteristics can be produced by the combination of various gas sensitive layers in a single sensor. For instance, by operating the gas sensor at various temperatures, the different temperature dependencies of the measurement sensitivity and the measurement characteristic of the various gas sensitive layers can be utilized in order to selectively determine different gas components in a gas mixture, in this case the gas-sensitive layer G. The electrical field is therefore limited to the region between the measuring electrodes D and the shielding electrode V, and as a result the vector of the electrical field intensity E (with the exception of the peripheral regions, which can be ignored) is orthogonal to the electrode surfaces. The current brought about in the electrical circuit by the voltage source $U_0$, which current is a measure for the gas concentration, and variations in this current, are displayed or indicated by the current meter SMG.

We claim:

1. A gas sensor, comprising:

a gas sensitive layer having two sides;

a measuring electrode structure on one of said sides of said gas sensitive layer; and an electrically conductive layer on the other of said sides of said gas sensitive layer said electrically conductive layer being constructed and positioned so as to electrically shield an electrical field above the measuring electrode structure.

2. The gas sensor according to claim 1, wherein said gas sensitive layer includes a substance selected from the group consisting of strontium titanate, barium titanate, vanadium oxide, gallium oxide, cerium oxide, barium stannate and zinc oxide.

3. The gas sensor according to claim 1, wherein said electrically conductive layer includes a catalytically active material.

4. The gas sensor according to claim 1, wherein said electrically conductive layer includes a substance selected from the group consisting of a metal oxide, a ceramic and an organic material.

5. The gas sensor according to claim 1, wherein said electrically conductive layer has a porous or perforated structure.

6. The gas sensor according to claim 1, including a heater.

7. The gas sensor according to claim 1, including a substrate carrying said measuring electrode structure, said gas sensitive layer, and said electrically conductive layer.

8. The gas sensor according to claim 7, including an insulation layer disposed between said measuring electrode structure and said substrate.

9. The gas sensor according to claim 1, including:

at least one further gas sensitive layer disposed above said electrically conductive layer; and at least one further electrically conductive layer disposed above said at least one further gas sensitive layer.

10. The gas sensor according to claim 9, wherein said at least one further gas sensitive layer includes a substance selected from the group consisting of strontium titanate, barium titanate, vanadium oxide, gallium oxide, cerium oxide, barium stannate and zinc oxide.

11. The gas sensor according to claim 9, wherein said at least one further electrically conductive layer includes a substance selected from the group consisting of a metal oxide, a ceramic and an organic material.

12. The gas sensor according to claim 9, wherein said at least one further electrically conductive layer has a porous or perforated structure.

13. The gas sensor according to claim 1, including a protective layer coating said gas sensitive layer and said electrically conductive layer.

14. The gas sensor according to claim 13, wherein said protective layer includes a substance selected from the group consisting of strontium titanate, barium titanate, vanadium oxide, gallium oxide, cerium oxide, barium stannate and zinc oxide.

15. The gas sensor according to claim 13, wherein said protective layer and said gas sensitive layer include the same material.

16. The gas sensor according to claim 13, including at least one further gas sensitive layer and at least one further electrically conductive layer disposed between said electrically conductive layer and said protective layer.

17. The gas sensor according to claim 16, wherein said at least one further gas sensitive layer includes a substance selected from the group consisting of strontium titanate, barium titanate, vanadium oxide, gallium oxide, cerium oxide, barium stannate and zinc oxide.

18. The gas sensor according to claim 16, wherein said at least one further electrically conductive layer includes a substance selected from the group consisting of a metal oxide, a ceramic and an organic material.

19. The gas sensor according to claim 16, wherein said at least one further electrically conductive layer has a porous or perforated structure.

* * * * *